(12) United States Patent
Bohannon et al.

(10) Patent No.: US 6,280,417 B1
(45) Date of Patent: Aug. 28, 2001

(54) TROCAR

(75) Inventors: Terry L. Bohannon; Lawrence W. Moser; Peter T. O'Heeron, all of Houston, TX (US); James Ogle, Midland, MI (US)

(73) Assignee: Needberg Technologies, Inc., Houston, TX (US)

( * ) Notice: Subject to any disclaimer, the term of this patent is extended or adjusted under 35 U.S.C. 154(b) by 0 days.

(21) Appl. No.: 09/256,009

(22) Filed: Feb. 23, 1999

(51) Int. Cl.$^7$ .................................................. A61M 5/178
(52) U.S. Cl. ............................. 604/164.06; 604/167.03; 604/165.01
(58) Field of Search .................. 604/264, 164.01, 604/164.02, 164.06, 165.01, 165.02, 165.04, 167.01, 167.03

(56) References Cited

U.S. PATENT DOCUMENTS

| | | |
|---|---|---|
| 4,535,773 | 8/1985 | Yoon . |
| 4,601,710 | 7/1986 | Moll . |
| 4,654,030 | 3/1987 | Moll et al. . |
| 4,902,280 | 2/1990 | Lander . |
| 4,931,042 | 6/1990 | Holmes et al. . |
| 5,030,206 | 7/1991 | Lander . |
| 5,104,382 * | 4/1992 | Brinkerhoff et al. . |
| 5,114,407 | 5/1992 | Burbank et al. . |
| 5,158,552 * | 10/1992 | Borgia et al. . |
| 5,256,147 | 10/1993 | Vidal et al. . |
| 5,275,583 | 1/1994 | Cranich . |
| 5,312,354 | 5/1994 | Allen et al. . |
| 5,350,393 | 9/1994 | Yoon . |
| 5,405,328 | 4/1995 | Vidal et al. . |
| 5,411,515 | 5/1995 | Haber et al. . |
| 5,431,635 | 7/1995 | Yoon . |
| 5,538,509 | 7/1996 | Dunlap et al. . |
| 5,549,564 | 8/1996 | Yoon . |
| 5,551,947 | 9/1996 | Kaali . |
| 5,554,137 | 9/1996 | Young et al. . |
| 5,554,167 | 9/1996 | Young et al. . |
| 5,569,289 | 10/1996 | Yoon . |
| 5,591,190 | 1/1997 | Yoon . |
| 5,607,440 | 3/1997 | Danks et al. . |
| 5,609,604 | 3/1997 | Schwemberger et al. . |
| 5,645,076 | 7/1997 | Yoon . |
| 5,645,556 | 7/1997 | Yoon . |
| 5,669,885 | 9/1997 | Smith . |
| 5,674,184 | 10/1997 | Hassler, Jr. . |
| 5,674,237 | 10/1997 | Ott . |
| 5,685,820 | 11/1997 | Riek et al. . |
| 5,697,947 | 12/1997 | Wolf et al. . |
| 5,720,761 | 2/1998 | Kaali . |
| 5,797,944 | 8/1998 | Nobles et al. . |
| 5,810,863 | 8/1998 | Wolf et al. . |
| B1 4,601,710 | 5/1998 | Moll . |

OTHER PUBLICATIONS

CORE Dnamics, Inc. "Disposable Trocoar and Reusable Automatic Valve Cannula System" Entree™ 1991.

* cited by examiner

*Primary Examiner*—Anhtuan T. Nguyen
*Assistant Examiner*—Jeremy Thissell
(74) *Attorney, Agent, or Firm*—McGlinchey Stafford, L.L.P.; Clarence E. Eriksen

(57) ABSTRACT

A trocar having a safety shield control mechanism that prevents the inner cannula from rotating and from moving axially when in the locked position. The safety shield control mechanism applies consistent pressure on the safety shield and has an open architecture for ease of sterilization. The trocar provides holding levels for different sizes of hands.

6 Claims, 4 Drawing Sheets

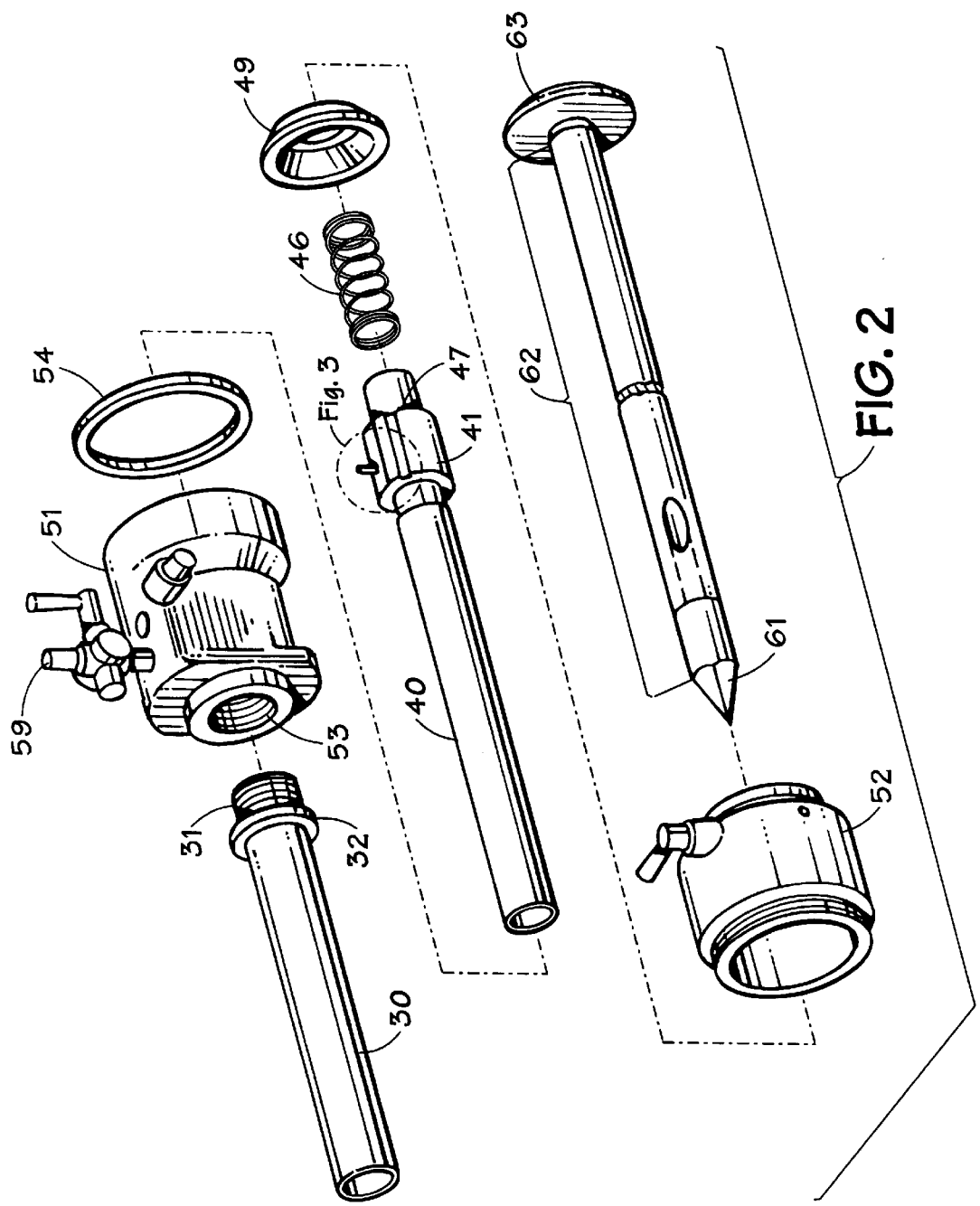

TROCAR

BACKGROUND OF THE INVENTION

1. FIELD OF THE INVENTION

The present invention relates to surgical instruments, and, more particularly, to trocars which are used to pierce or puncture an anatomical cavity to provide communication with the inside of the cavity during a surgical procedure.

2. DESCRIPTION OF THE PRIOR ART

Endoscopic surgery, and in particular laparoscopic surgery, constitutes a significant method for performing surgeries and has become the surgical procedure of choice, because of its patient care advantages over "open surgery." In particular, a significant advantage of laparoscopic surgery over open surgery is the decreased post-operative recovery time. In most instances, a patient is able to leave the hospital within hours after laparoscopic surgery has been performed, as compared to the multi-day hospitalization necessary to recover from open surgical procedures. Further, laparoscopic surgery provides decreased incidents of post-operative abdominal adhesions and decreased post-operative pain. Cosmetic results are also enhanced with laparoscopic surgery.

A trocar is an essential medical instrument for use in laparoscopic surgery, because it is used to puncture the wall of an anatomical cavity. A trocar includes a tube or cannula and a sharp, generally pointed cutting element called an obturator. The obturator fits within the cannula and has a sharp piercing tip at its end.

Conventionally, a laparoscopic trocar insertion procedure is preceded by the insufflation of the abdominal cavity with carbon dioxide. The introduction of this gas into the abdominal cavity lifts the abdominal wall away from the internal viscera. The abdominal wall is then penetrated with the trocar, and after insertion of the trocar through the abdominal wall, the obturator is removed by the surgeon, leaving the cannula or tube protruding through the body wall. Laparoscopic instruments can then be inserted through the cannula to view internal organs or to perform surgical procedures.

Penetrating the wall of the abdominal cavity with the trocar is done relatively quickly, and while the obturator encounters a fair amount of resistance from the skin muscle and tissue membranes of the abdominal wall, the resistance to the trocar drops quickly once the cutting element passes through the abdominal wall. Within the abdominal cavity, the sharp point of the cutting element may easily injure or cut an internal organ upon the slightest of contacts. Accordingly, many trocars include a safety shield that snaps forward to cover the sharp point of the obturator, once the trocar has penetrated the abdominal wall. Preferably, the safety shield is locked into place once the abdominal wall has been penetrated, and cannot be unlocked absent positive intervention by the surgeon.

While locking safety shields for trocars have been available, the locking mechanisms employed in these trocars has suffered from the disability that consistent pressure is not placed on the safety shield. Further, the architecture of locking mechanisms in the prior art trocars has not been open, which has made those trocars difficult to sterilize.

Despite the fact that trocars are hand-held instruments, prior art trocars have been less than ergonomically friendly to the user. Rather, prior art trocars have suffered from the disability of being difficult to control, since they are not designed to provide for a plurality of hand positions or for different holding levels that allow for different size hands to manipulate the trocar.

The foregoing and other shortcomings of prior art trocars have been overcome by the trocar of the present invention.

SUMMARY OF THE INVENTION

A trocar in accordance with the present invention comprises a body assembly and a cannula assembly. The cannula assembly includes an outer cannula attached to the body assembly to define a bore therethrough and an inner cannula inserted in said bore; wherein the inner cannula has a length longer than the length of the outer cannula.

The trocar body includes a safety shield control mechanism having locked position and an unlocked position which is activated during surgical insertion of the trocar. This control mechanism includes a mounting mechanism which is attached to the trocar inside the body assembly to prevent not only rotation of the inner cannula, but also axial movement of the inner cannula in the locked position. The safety shield control mechanism also includes a trigger mechanism for placing the safety shield control mechanism in the unlocked position to allow limited axial movement of the inner cannula.

A trocar in accordance with the present invention also includes an obturator assembly in the bore of the trocar. The obturator has a sharp end which is shielded by the inner cannula when the safety shield control mechanism is in the locked position. The sharp end of the obturator becomes exposed during surgical insertion of the trocar when the safety shield control mechanism is in the unlocked position.

The mounting mechanism in the safety shield control mechanism includes a mounting bracket having vertical ribs and the inner cannula has axial slots for engagement with said vertical ribs to prevent rotation of the inner cannula. The mounting mechanism also has a locking arm assembly comprising two spring-loaded locking arms for engaging the proximal end of the inner cannula to prevent axial movement of the inner cannula in the locked position.

The trigger mechanism of the safety shield control mechanism includes apparatus for moving the locking arm assembly to an unlocked position to allow limited axial movement of the inner cannula toward the rear of the trocar. In a preferred embodiment the trigger mechanism comprises a plunger-like button shaft which extends from the outside of the trocar body to the inside of the trocar body. The portion of the button shaft which is outside the trocar body has an end for threaded engagement with a spring-loaded cap. The portion of the button shaft on the inside of the trocar body has a tapered end which is slidably engaged in a hole in the locking arm assembly to move the locking arm assembly to the unlocked position when the spring-loaded cap is depressed.

A trocar in accordance with the present invention also includes a spring-loaded flapper valve assembly which is located inside the trocar body assembly at the rear of the trocar body assembly. This flapper valve assembly closes to seal the bore of the trocar when the obturator assembly is removed from this trocar.

A trocar in accordance with the present invention is fabricated to provide two holding levels to accommodate different size hands.

BRIEF DESCRIPTION OF THE DRAWINGS

In the accompanying drawings:

FIG. 2 is an exploded drawing of a trocar in accordance with the present invention.

DETAILED DESCRIPTION OF THE INVENTION

It will be appreciated that the present invention can take many forms and embodiments. Some embodiments of the invention are described so as to give an understanding of the invention. The embodiments described herein are intended to be illustrative, and not limiting, of the present invention.

Figure 1:
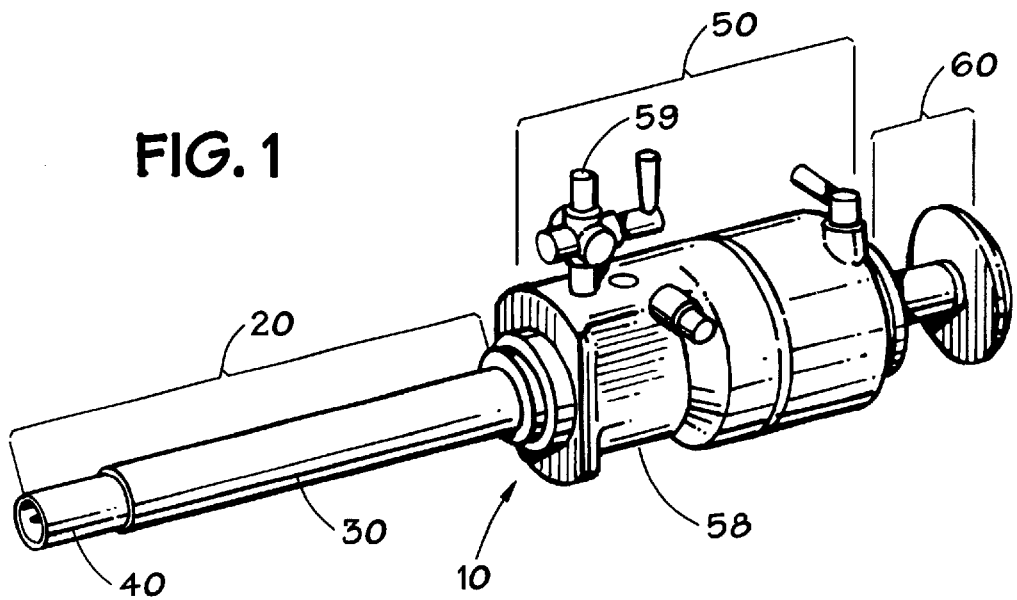
FIG. 1 is a perspective drawing of a trocar in accordance with the present invention.

With reference first to FIG. 1, a perspective view of a trocar assembly 10 in accordance with the present invention is illustrated. Trocar assembly 10 includes a cannula subassembly 20 comprising outer cannula 30 and inner cannula 40, each of which is a tubular member. Trocar assembly 10 further includes trocar body subassembly 50 which is described in more detail below and obturator subassembly 60. In FIG. 1, inner cannula 40 is in its extended position which results in the pointed or sharp end 61 of obturator subassembly 60 being shielded by the distal end of inner cannula 40.

With reference to FIG. 2, the proximal end of outer cannula 30 is attached to lower trocar body 51, and a variety of different methods exist that are well known to those skilled in the art for effecting such attachment. Preferably, however, lower trocar body 51 has a threaded bore 53 for receiving the threaded proximal end 31 of outer cannula 30 so that outer cannula 30 is removable from lower trocar body 51. Stop flange 32 limits the extent of threaded engagement between inner cannula 30 and lower trocar body 51. The outer cannula 30 and lower trocar body 51 align to have a central axial bore for receiving the inner cannula 40 and the obturator subassembly 60. The central bore is larger in the lower trocar body 51 than in the outer cannula.

The inner cannula 40 is a tube adapted to be slidably inserted through the bore in lower trocar body 51 and into outer cannula 30. Cylinder 41 is press fit on the inner cannula 40 near its proximal end and the diameter of cylinder 41 is larger than the diameter of the bore of lower trocar body 51, which prevents inner cannula 40 from sliding completely through lower trocar body 51.

Figure 3:
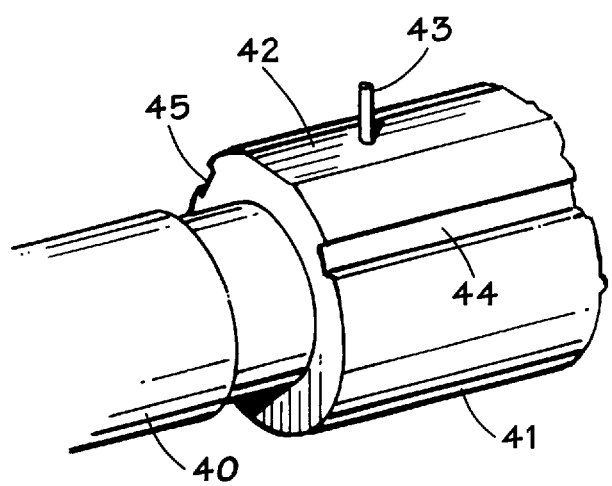
FIG. 3 is a perspective drawing of a portion of the proximal end of the inner cannula depicted in FIGS. 1 and 2.
Figure 6:
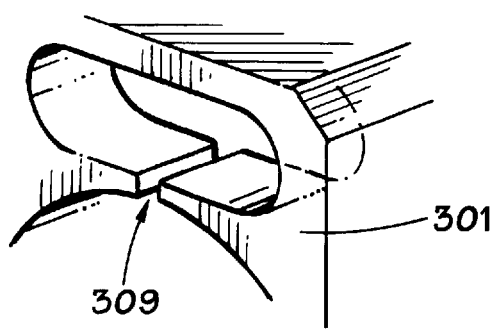
FIGS. 5–7 are perspective drawings of various aspects of the safety shield mechanism of FIG. 4.

With reference to both FIGS. 2 and 3, a portion 42 of the surface area of cylinder 41 is flattened, and a guide pin 43 is installed in the flattened portion 42 perpendicular to the flattened portion 42. Also, two axial slots 44 and 45 are formed in cylinder 41. The two axial slots 44 and 45 in cylinder 41 are circumferentially spaced the same distance from flattened portion 42. The guide pin 43 and the two axial slots 44 and 45 engage and cooperate with the safety shield control mechanism as described below.

An annular space 47 is defined between cylinder 41 and the proximal end of outer cannula 40, and one end of spring 46 slips over the proximal end of outer cannula 40 and into this annular space. The other end of spring 46 engages spring retaining washer 49, which also has a bore therethrough and which fits into upper trocar body 52 of trocar body subassembly 50. Upper trocar body 52 is attached to lower trocar body 51 by threaded engagement, thereby permitting upper trocar body 52 to be removed from lower trocar body 51. Gasket 54 is interposed between upper and lower trocar bodies.

The obturator subassembly 60 includes a pyramidal-shaped knife 61, and a elongated stem or shaft 62, and an arcuate-shaped cap 63. The obturator subassembly 60 is adapted to extend and move longitudinally through upper trocar body 52 and inner cannula 30. As noted above, inner cannula 40 serves as a safety shield for the knife 61 when the inner cannula is in the extended position as shown in FIG. 1. The obturator subassembly 60 may be easily removed from the trocar assembly.

Figure 8:
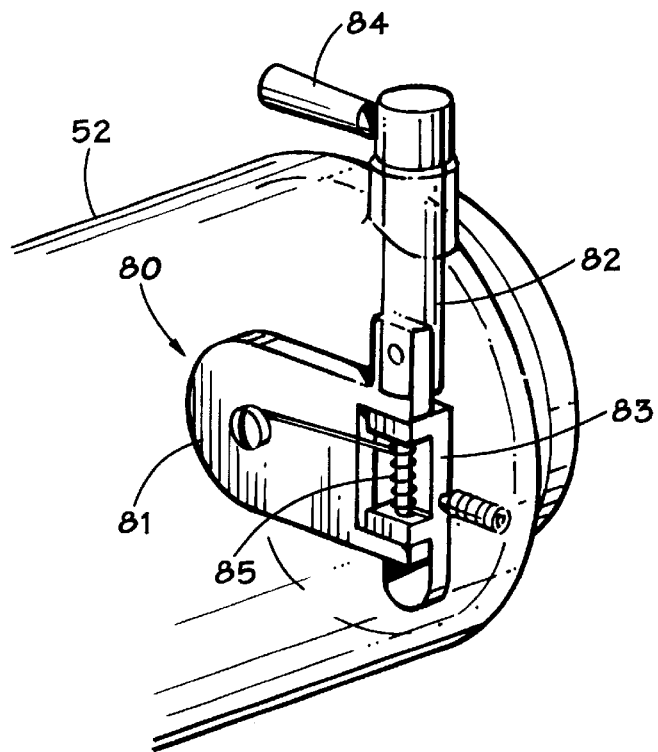
FIGS. 8 and 9 are perspective drawings of the flapper valve assembly of a trocar in accordance with the present invention.
Figure 9:
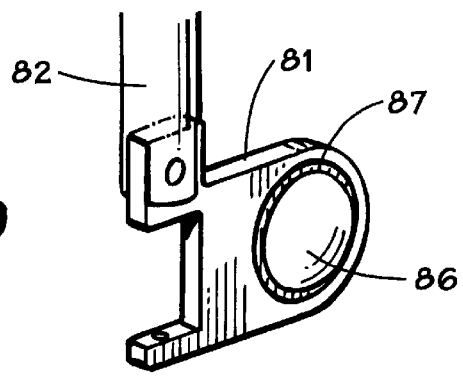

With reference now to FIGS. 8 and 9, the rearmost position of upper trocar body 52 includes a flapper valve assembly 80, having a valve door 81 and a valve handle assembly 82. A slot 83 is milled in upper trocar body 52 for receiving the lower portion of valve handle assembly 82, and the upper portion of valve handle assembly terminates outside of upper trocar body 52 and has a handle 84. The flapper valve assembly 80 is spring-mounted using spring 85. The portion of valve door 81 that faces to the rear of upper trocar body 52 has a dome-shaped central portion 86 which is surrounded at its base by circular-shaped gasket 87. The valve door 81 may be opened by turning handle 84 counter-clockwise or by insertion of the obturator assembly 60 into the bore in upper trocar body 52. When the obturator assembly 60 is removed from the trocar, spring 85 causes valve door 81 to close and gasket 87 functions as a seal to minimize the escape of gas that has been introduced into the patient's abdomen.

The axial position of the inner cannula 40 in the trocar assembly is controlled by a safety shield control or snap back mechanism which is located in the lower trocar body 51 and which is removably engaged with the inner cannula 40. As described in more detail below, positive intervention by the surgeon is required to activate the safety shield control mechanism. When this mechanism is activated, inner cannula 40 is permitted to move axially inward toward the housing assembly to expose the sharp tip of obturator assembly 60. This safety shield control mechanism provides visual and aural signals to the surgeon respecting engagement and disengagement of the inner cannula 40 as a safety shield for the pointed or sharp end. When the trocar cannula subassembly 20 and safety shield control mechanism 53 are properly coupled, operation of the inner cannula 40 as a safety shield can be verified without the obturator subassembly 60 being inserted in the trocar.

Figure 4:
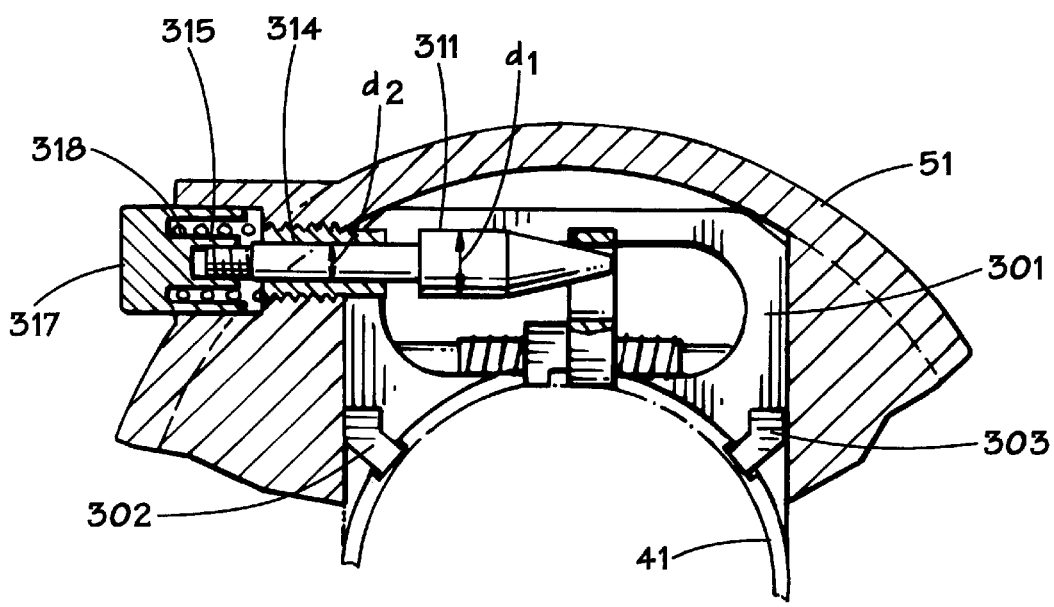
FIG. 4 is a top view lower trocar body shown in FIG. 2 which illustrates the safety shield control mechanism in a trocar in accordance with the present invention.
Figure 5:
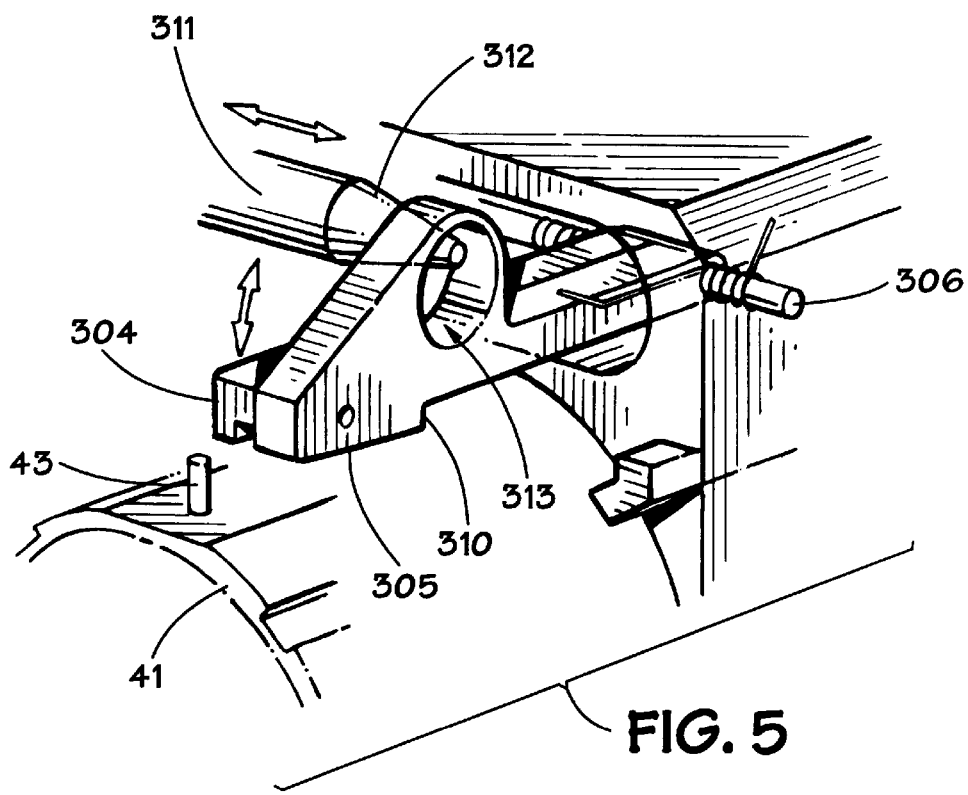
Figure 7:
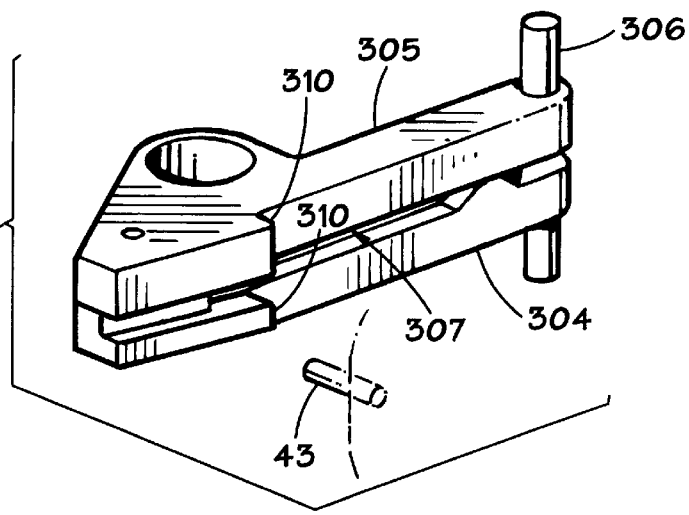

With reference to FIGS. 4–7, the safety shield control or snap back mechanism of a trocar in accordance with the present invention comprises a mounting bracket 301, having two vertical ribs 302 and 303. These vertical ribs 302 and 303 are engaged by the axial slots 44 and 45, respectively, formed in cylinder 41 of inner cannula 40. The safety shield control mechanism of FIGS. 4–7 also includes two locking arms 304 and 305 which are rotably mounted to mounting bracket 301 on shaft 306 and the position of locking arms 304, 305 is spring-biased toward the bore of the trocar. As shown in FIG. 7, locking arms 304 and 305 are machined such that an axial space 307 exists between them, and axial space 307 lines up with space 309 in mounting bracket 301. Locking arms 304 and 305 are joined together at their tops by a dowel pin (not shown) in arm 304 which fits into a hole formed in arm 305. The safety shield control mechanism is installed in and attached to the barrel of lower trocar body 51 as shown in FIG. 4 and this attachment is made using a bolt.

To install the inner cannula 40 in the trocar, axial slots 44 and 45 engage vertical ribs 302 and 303 and guide pin 43 moves in the space defined by slots 309 and 307. The inner cannula 40 is then pushed forward until the lip 310 of locking arms 304 and 305 is on top of the proximal end of inner cannula 40. Inner cannula 40 is prevented from rotating by the engagement of the vertical ribs 302 and 303 with axial slot 44 and 45 and is prevented from moving axially by locking arms 304 and 305.

The safety shield mechanism also has a trigger mechanism comprising a button shaft having one portion 311 with a diameter $d_1$, and a second portion 314 with a smaller diameter $d_2$. The button shaft is held in lower trocar body 51 by a button bushing 315. The button shaft has a tapered end 312 that engages the opening 313 in locking arm 305. The second portion 314 of the button shaft has a threaded end to engage the corresponding threads in cap 317. A spring 318 is interposed between cap 317 and button bushing 315.

The safety shield mechanism is activated as follows. When the trocar is to be inserted into the patient, the distal end of inner cannula 40 is brought into contact with the patient's abdomen. The trigger mechanism is then activated by depressing cap 317, which causes the button shaft to move to the right in FIG. 4. As the tapered portion of the button shaft moves to the right in FIG. 4, arms 304 and 305 move away from the bore of the trocar, thereby releasing inner cannula 40 from its locked position. As the surgeon pushes on the trocar to insert it into the patient, the force on the inner cannula 40 from the patient's abdominal wall causes the inner cannula 40 to move rearward, thereby exposing the sharp end of the obturator assembly 60. The extent of this rearward movement is controlled by guide pin 43 and slots 307 and 309. When the sharp end of the obturator assembly 60 and the inner cannula 40 pass through the abdominal wall of the patient, the trocar encounters decreased resistance. At this time, the spring 46 causes inner cannula 40 to snap back to its extended position as shown in FIG. 1, and the inner cannula 40 thus shields the sharp end of the obturator assembly.

With reference again to FIG. 1, a trocar in accordance with the present invention provides two holding levels for different size hands. The trocar may be grasped by smaller sized hands where the cannula sub-assembly engages the trocar body subassembly. Alternatively, the trocar may be grasped by larger sized hands at grove 58.

Lastly, a trocar in accordance with the present invention includes stop cock 59 which is threadably engaged in lower trocar body 51. A source of carbon dioxide(not shown) is connected to stop cock 59 to maintain the level of insufflation of the abdominal cavity during the laparoscopic procedure.

What is claimed is:

1. A trocar, comprising:
   (a) a body assembly;
   (b) a cannula assembly comprising an outer cannula attached to body assembly to define a bore therethrough and an inner cannula which is inserted in the bore and which may move axially from an extended position to a retracted position, the inner cannula having a length which is greater than the length of the outer cannula;
   (c) an obturator assembly in the bore of the trocar, the obturator assembly having a sharp end which is shielded by the inner cannula when the inner cannula is in the extended position and which becomes exposed during surgical insertion of the trocar when the inner cannula is in the retracted position; and
   (d) an inner cannula control mechanism in the body assembly, which inner cannula control mechanism has a locked position and an unlocked position and which inner cannula control mechanism is activated during surgical insertion of the trocar, comprising:
      (i) a mounting mechanism which is attached to the trocar inside the body assembly to prevent rotation of the inner cannula and to prevent axial movement of the inner cannula when in the locked position, said mounting mechanism including two spring-loaded locking arms which, in the locked position, directly engage the proximal end of the inner cannula to lock the inner cannula in its extended position;
      (ii) a trigger mechanism which moves the locking arms away from direct engagement with the inner cannula to place the inner cannula control mechanism in the unlocked position to allow limited rearward axial movement of the inner cannula.

2. The trocar of claim 1, wherein the mounting mechanism includes a mounting bracket having vertical ribs and wherein the inner cannula has axial slots for engagement with said vertical ribs to prevent rotation of the inner cannula.

3. The trocar of claim 1, wherein the trigger mechanism comprises a plunger-like button shaft which extends from the outside of the trocar body to the inside of the trocar body, the portion of the button shaft which is outside the trocar body having an end for threaded engagement with a spring-loaded cap and the portion of the button shaft on the inside of the trocar body having a tapered end which is slidably engaged in a hole in the locking arm assembly to move the locking arm assembly to the unlocked position when the spring-loaded cap is depressed.

4. The trocar of claim 1, further comprising a spring-loaded flapper valve assembly which is located inside the trocar body assembly at the rear of the trocar body assembly and which closes to seal the bore of the trocar when the obturator assembly is removed from this trocar.

5. The trocar of claim 1, wherein the trocar body assembly is fabricated to provide two holding levels to accommodate different size hands.

6. The trocar of claim 1, further comprising a spring in the body assembly which is compressed by the rearward axial movement of the inner cannula and which forces the inner cannula to snap back into its extended position when the trocar is surgically inserted in a patient.

* * * * *

UNITED STATES PATENT AND TRADEMARK OFFICE
CERTIFICATE OF CORRECTION

PATENT NO. : 6,280,417 B1
DATED : August 28, 2001
INVENTOR(S) : Terry L. Bohannon et al.

It is certified that error appears in the above-identified patent and that said Letters Patent is hereby corrected as shown below:

Title page,
Item [73], after "Assignee", please delete "Needberg" and insert -- NeoSurg --.

Signed and Sealed this

Twenty-sixth Day of February, 2002

Attest:

JAMES E. ROGAN
Attesting Officer
Director of the United States Patent and Trademark Office